(12) United States Patent
Bhat et al.

(10) Patent No.: US 6,503,954 B1
(45) Date of Patent: Jan. 7, 2003

(54) BIOCOMPATIBLE CARRIER CONTAINING ACTINOMYCIN D AND A METHOD OF FORMING THE SAME

(75) Inventors: Vinayak D. Bhat, Sunnyvale; Syed F. A. Hossainy, Fremont; Daryush Mirzaee, Sunnyvale; Evgenia Mandrusov, Campbell; Deborra Sanders-Millare; Judy A. Guruwaiya, both of San Jose, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/621,123

(22) Filed: Jul. 21, 2000

Related U.S. Application Data (63) Continuation-in-part of application No. 09/540,242, filed on Mar. 31, 2000, now abandoned.

(51) Int. Cl.[7] .................. A61K 47/30; A61K 47/32; A61K 47/34

(52) U.S. Cl. ............... 514/772.2; 424/78.08; 424/422; 424/423; 424/424; 424/484; 424/486; 623/1.42; 623/1.14; 623/1.15; 427/2.1

(58) Field of Search .................. 623/1.42, 1.14, 623/1.15; 424/78.06, 78.08, 422, 423, 424, 484, 486; 606/231; 427/2.1; 514/772.2

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,977,901 A | 12/1990 | Ofstead | 128/772 |
| 5,328,471 A | 7/1994 | Slepian | 604/101 |
| 5,464,650 A | * 11/1995 | Berg et al. | 427/2.3 |
| 5,578,073 A | * 11/1996 | Haimovich | 623/1.43 |

(List continued on next page.)

FOREIGN PATENT DOCUMENTS

| | | |
|---|---|---|
| EP | 0301856 | 5/1995 |
| EP | 0 665 023 | 8/1995 |
| EP | 0 970 711 | 1/2000 |
| WO | WO 91/12846 | 9/1991 |
| WO | 96/40174 | 12/1996 |
| WO | WO 97/45105 | 12/1997 |
| WO | 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 | 1/2001 |
| WO | WO 01/45763 | 6/2001 |

OTHER PUBLICATIONS

Chem: Abstract 125:212307 T. Shigeno 1996.*
Barath, et al.; *Low Dose of Antitumor Agents Prevents Smooth Muscle Cell Proliferation After Endothelial Injury*; JACC vol. 13, No. 2; Feb. 1989:252A (Abstract).

(List continued on next page.)

*Primary Examiner*—Thurman K. Page
*Assistant Examiner*—Liliana Di Nola-Baron
(74) *Attorney, Agent, or Firm*—Squire, Sanders & Dempsey, L.L.P.; Cameron K. Kerrigan, Esq.

(57) ABSTRACT

A biocompatible carrier and a composition for forming the carrier are disclosed. The carrier is made from an ethylene vinyl alcohol copolymer which can serve as a reservoir, allowing for the local delivery and sustained release of actinomycin D. The carrier can be formed from the ethylene vinyl alcohol, copolymer, a dimethylsulfoxide solvent, and actinomycin D. Alternatively, the carrier can be formed from an ethylene vinyl alcohol copolymer, a dimethylsulfoxide solvent, actinornycin D, and a wetting fluid. The carrier can serve as a coating for a prosthesis, for example a stent. The composition is applied to a surface of the prosthesis and essentially all of the dimethylsulfoxide solvent or dimethylsulfoxide solvent/wetting fluid is removed or allowed to evaporate to form the coating.

30 Claims, 3 Drawing Sheets

U.S. PATENT DOCUMENTS

| | | | |
|---|---|---|---|
| 5,605,696 A | | 2/1997 | Eury et al. .................. 424/423 |
| 5,628,730 A | | 5/1997 | Shapland et al. ............. 604/21 |
| 5,667,767 A | | 9/1997 | Greff et al. .............. 424/9.411 |
| 5,670,558 A | | 9/1997 | Onishi et al. ............... 523/112 |
| 5,700,286 A | | 12/1997 | Tartaglia et al. ............... 623/1 |
| 5,716,981 A | | 2/1998 | Hunter et al. ............... 514/449 |
| 5,800,392 A | | 9/1998 | Racchini ..................... 604/96 |
| 5,824,049 A | | 10/1998 | Ragheb et al. ................. 623/1 |
| 5,830,178 A | | 11/1998 | Jones et al. ................... 604/49 |
| 5,837,313 A | | 11/1998 | Ding et al. ................ 427/2.21 |
| 5,851,508 A | | 12/1998 | Greff et al. .............. 424/9.411 |
| 5,865,814 A | | 2/1999 | Tuch .......................... 604/265 |
| 5,873,904 A | | 2/1999 | Ragheb et al. ................. 623/1 |
| 5,971,954 A | * | 10/1999 | Conway et al. ............. 604/921 |
| 5,980,928 A | * | 11/1999 | Terry .......................... 623/1.42 |
| 5,980,972 A | | 11/1999 | Ding .......................... 427/2.24 |
| 6,010,530 A | | 1/2000 | Goiceochea ................... 623/1 |
| 6,015,541 A | | 1/2000 | Greff et al. ................. 424/1.25 |
| 6,096,070 A | | 8/2000 | Ragheb et al. ................. 623/1 |
| 6,153,252 A | * | 11/2000 | Hossainy et al. ............ 427/2.3 |
| 6,165,212 A | | 12/2000 | Dereume et al. .......... 623/1.13 |
| 6,258,121 B1 | | 7/2001 | Yang et al. ................ 623/1.46 |

OTHER PUBLICATIONS

Matsumaru, et al.; *Embolic Materials For Endovascular Treatment of Cerebral Lesions*; J. Biomater. Sci. Polymer Edn, vol. 8, No. 7 (1997), pp. 555–569.

Miyazaki, et al., "*Antitumor Effect of Implanted Ethylene–Vinyl Alcohol Copolymer Matrices Containing Anticancer Agents on Ehrlich Ascites Carcinoma and P388 Leukemia in Mice,*" Chem. Pharm. Bull. 33(6)2490 (1985), pp. 2490–2498.

Miyazawa et al.; *Effects of Pemirolast and Tranilast on Intimal Thickening After Arterial Injury in the Rat*; J. Cardiovasc. Pharmacol. (1997), pp. 157–162.

Ohsawa, et al.; *Preventive Effects of an Antiallergic Drug, Pemirolast Potassium, on Restenosis After Percutaneous Transluminal Coronary Angioplasty*; American Heart Journal (Dec. 1998); pp. 1081–1087.

Dichek et al., *Seeding of Intravascular Stents with Genetically Engineered Endothelial Cells*, Circ. 80(5):1347–1353 (1989).

* cited by examiner

BIOCOMPATIBLE CARRIER CONTAINING ACTINOMYCIN D AND A METHOD OF FORMING THE SAME

CROSS-REFERENCE

This is a continuation-in-part of U.S. patent application Ser. No. 09/540,242, filed on Mar. 31, 2000, and is a continuation-in part of U.S. patent application Ser. No. 09/470,559, filed on Dec. 23, 1999, which is a continuation-in-part of U.S. patent application Ser. Nos. 09/390,855, filed Sep. 3, 1999 and U.S. Pat. No. 09/390,069, filed Sep. 3, 1999.

BACKGROUND OF THE INVENTION

1. Field of the Invention

This invention relates to a biocompatible carrier containing an active ingredient for introducing the active ingredient to certain target cell population in a vascular region, such as smooth muscle cells, requiring modulation to ameliorate a diseased state, particularly for the treatment of stenosis or restenosis following a vascular trauma or disease. Moreover, the invention is directed to a composition, for coating an implantable device, containing actinomycin D, or analogs and derivatives thereof.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an expandable, intraluminal prosthesis, one example of which includes a stent, is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents, although a significant innovation in the treatment of occlusive regions, has not reduced the development of restenosis.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents disclosed seeding the stents with endothelial cells (Dichek, D. A. et al. Seeding of Intravascular Stents With Genetically Engineered Endothelial Cells; Circulation 1989; 80: 1347–1353). Briefly, endothelial cells were seeded onto stainless steel stents and grown until the stents were covered. The cells were therefore able to be delivered to the vascular wall where they provided therapeutic proteins. Another proposed method of providing a therapeutic substance to the vascular wall included use of a heparin-coated metallic stent, whereby a heparin coating was jonically or covalently bonded to the stent. Significant disadvantages associated with the aforementioned methods include significant loss of the therapeutic substance from the body of the stent during delivery and expansion of the stent, and an absolute lack of control of the release rate of the therapeutic substance from the stent.

Another proposed method involved the use of a polymeric carrier coated onto the surface of a stent, as disclosed in U.S. Pat. No. 5,464,650 issued to Berg et al. Berg disclosed applying to a stent body a solution which included a specified solvent, a specified polymer dissolved in the solvent, and a therapeutic substance dispersed in the blend. The solvent was allowed to evaporate, leaving on the stent surface a coating of the polymer and the therapeutic substance impregnated in the polymer. Among the specified, suitable choices of polymers listed by Berg, empirical results were specifically provided for poly(caprolactone) and poly (L-lactic acid). The preferred choice of mutually compatible solvents included acetone or chloroform. As indicated by Berg, stents where immersed in the solution 12 to 15 times or sprayed 20 times. The evaporation of the solvent provided a white coating. A white coloration is generally indicative of a brittle polymeric coating. A brittle polymeric coating is an undesirable characteristic, since portions of the coating typically become detached during stent expansion. Detachment of the coating causes the quantity of the therapeutic substance to fall below a threshold level sufficient for the effective treatment of a patient.

Accordingly, it is desirable to provide an improved coating that is susceptible to expanding with a prosthesis without significant detachment from the surface of the prosthesis. It is also desirable for the polymer to be able to strongly adhere to the surface of the prosthesis, thereby preventing loss of the polymeric coating during prosthesis delivery. Other desirable features include, but are not limited to, a polymeric coating which allows for a significant control of the release rate of a therapeutic substance, a polymeric solution which need not be applied excessively to the surface of the prosthesis to form a coating of a suitable thickness, and a polymeric solution that can be uniformly applied to the surface of the prosthesis.

Local administration of therapeutic agents via stents has shown some favorable results in reducing restenosis. However, development of restenosis remains a persistent problem which has not been significantly alleviated by therapeutic substances which are currently used in the market. Accordingly, there is a great need for better and more effective therapeutic compositions, and method of administering the compositions, for inhibiting smooth muscle cell hyper-proliferation for the effective treatment of restenosis.

SUMMARY OF THE INVENTION

In accordance with one embodiment of the invention a coating for a prosthesis is provided. In one embodiment, the coating comprises an ethylene vinyl alcohol copolymer and actinomycin D or analogs or derivatives thereof. In another embodiment, the coating additionally comprises a therapeutic agent used in combination with actinomycin D or analogs or derivatives thereof The prosthesis can be a balloon-expandable stent, a self-expandable stent or a graft.

In accordance with another embodiment, a method for forming a coating onto a surface of a prosthesis, e.g., a stent, is provided. In one embodiment, the method comprises applying to the surface of the prosthesis a composition which includes an ethylene vinyl alcohol copolymer and actinomycin D, or analogs or derivatives thereof. In another embodiment, the composition additionally includes a therapeutic agent used in combination with the actinomycin D.

The composition can include a fluid. In one embodiment the fluid is a dimethylsulfoxide solution. The ethylene vinyl alcohol copolymer can constitute from about 0.1% to about 35%, the dimethylsulfoxide solution can constitute from about 59.9% to about 99.8%, and the actinomycin D, alone or in combination with the therapeutic agent, can constitute from about 0.1% to about 40% by weight of the total weight of the composition.

In accordance with another embodiment, the fluid can include the dimethylsulfoxide solution and a wetting fluid. To enhance the wetting of the composition, a suitable wetting fluid typically has a high capillary permeation. A suitably high capillary permeation corresponds to a contact angle less than about 90°. The wetting fluid can have a viscosity not greater than about 50 centipoise. The wetting fluid, accordingly, when added to the composition, reduces the viscosity of the composition. The wetting fluid should be mutually compatible with the ethylene vinyl alcohol copolymer, dimethylsulfoxide solution, and actinomycin D and should not precipitate the copolymer. Useful examples of the wetting fluid include, but are not limited to, tetrahydrofuran (THF), dimethylfornamide (DMF), 1-butanol, n-butyl acetate, dimethyl acetamide (DMAC), and mixtures thereof. In this embodiment, the ethylene vinyl alcohol copolymer can constitute from about 0.1% to about 35%, the dimethylsulfoxide can constitute from about 19.8% to about 98.8%, the wetting fluid can constitute from about 1% to about 80%, and the actinomycin D, alone or in combination with a therapeutic agent, can constitute from about 0.1% to about 40% by weight of the total weight of the composition.

The composition can be applied to the prosthesis simply by immersing the prosthesis into the composition or by spraying the composition onto the surface of the prosthesis. The dimethylsulfoxide solution or the combination of the dimethylsulfoxide solution and wetting fluid is removed from the composition which is applied to the surface of the prosthesis. The copolymer and the actinomycin D, alone or in combination with a therapeutic agent, solidifies and adheres to the surface of the prosthesis. One technique for removing the dimethylsulfoxide solution or combination of the dimethylsulfoxide solution and wetting fluid includes allowing the components to evaporate to a substantial elimination, for example, by heating the prosthesis at a predetermined temperature for a predetermined duration of time.

In accordance with another embodiment, a composition is provided for treating or inhibiting the narrowing of the blood vessel. The composition includes ethylene vinyl alcohol copolymer and actinomycin D, or analogs and derivatives thereof. The therapeutic composition is capable of being deposited in a selected region of the blood vessel to treat or inhibit the narrowing of the blood vessel.

In accordance with another embodiment, a therapeutic method is provided for inhibiting restenosis of a blood vessel by deposition into a designated region of the blood vessel an ethylene vinyl alcohol copolymer carrier impregnated with actinomycin D, or analogs and derivatives thereof.

DETAILED DESCRIPTION OF THE EMBODIMENTS

Composition

The embodiments of the composition are prepared by conventional methods wherein all components are combined, then blended. More particularly, in accordance to one embodiment, a predetermined amount of an ethylene vinyl alcohol copolymer (commonly known by the generic name EVOH or by the trade name EVAL) is added to a predetermined amount of a dimethylsulfoxide (DMSO) solvent at ambient pressure and under anhydrous atmosphere. If necessary, gentle heating and stirring and/or mixing can be employed to effect dissolution of the copolymer into the DMSO solvent, for example 12 hours in a water bath at about 60° C.

Ethylene vinyl alcohol copolymer refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 44%. Typically, 44 mole percent ethylene is suitable. As a general rule, an increase in the amount of the ethylene comonomer content decreases the rate that a therapeutic substance is released from the matrices of the copolymer. The release rate of a therapeutic substance decreases as the hydrophilicity of the polymer decreases. An increase in the amount of the ethylene comonomer content decreases the hydrophilic nature of vinyl alcohol comonomer. Ethylene vinyl alcohol copolymers are available commercially from companies such as Aldrich Chemical Company, Milwaukee, Wis., or EVAL Company of Aerica, Lisle, Ill., or can be prepared by conventional polymerization procedures that are well known to one of ordinary skill in the art. Typically, the ethylene vinyl alcohol copolymer can comprise from about 0.1% to about 35%, usefully from about 12% to about 20% by weight of the total weight of the composition. Typically, the DMSO solvent can comprise from about 65% to about 99.9%, usefully from about 80% to about 88% by weight of the total weight of the composition. A specific weight ratio is dependent on factors such as the material from which the prosthesis is made and the geometrical structure of the prosthesis.

Figure 1A:
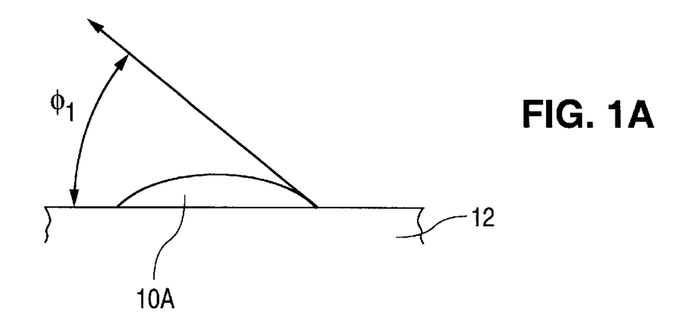
FIG. 1A illustrates a fluid on a solid substrate having a contact angle $\Phi_1$.
Figure 1B:
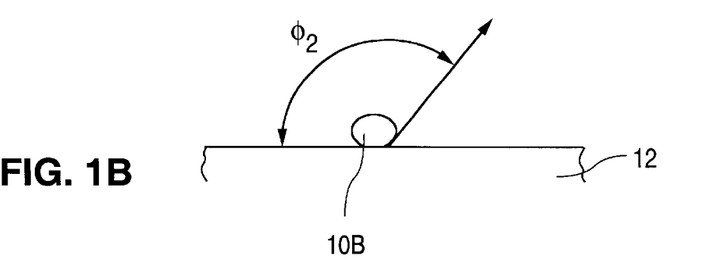
FIG. 1B illustrates a fluid on a solid substrate having a contact angle $\Phi_2$.

In accordance with another embodiment, a fluid can be added to the composition which can enhance the wetting of the composition. To enhance the wetting of the composition, a suitable fluid typically has a high capillary permeation. Capillary permeation or wetting is the Imovement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 1A illustrates a fluid droplet 10A on a solid substrate 12, for example a stainless steel surface. Fluid droplet 10A has a high capillary permeation that corresponds to a contact angle $\Phi_2$, which is less than about 90°. In contrast, FIG. 1B illustrates a fluid droplet 10B on solid substrate 12, having a low capillary permeation that corresponds to a contact angle $\Phi_2$, which is greater than about 90°. The wetting fluid, typically, should have a viscosity not greater than about 50 centipoise, usefully about 0.3 to about 5 centipoise, more usefully about 0.4 to about 2.5 centipoise, in room temperature. The wetting fluid, accordingly, when added to the composition, reduces the viscosity of composition. The wetting fluid should be mutually compatible with the ethylene vinyl alcohol copolymer and DMSO solvent and should not precipitate the copolymer. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof. In this embodiment, the ethylene vinyl alcohol copolymer can comprise from about 0.1% to about 35%, usefully from about 10% to about 25% by weight of the total weight of the composition. The DMSO solvent can comprise from about 19.9% to about 98.9%, usefully from about 50% to about 79% by weight of the total weight of the composition. The wetting fluid can comprise from about 1% to about 80%, usefully from about 5% to about 40% by weight of the total weight of the composition. The specific weight ratio of the wetting fluid depends on the type of wetting fluid employed and the weight ratio of the ethylene vinyl alcohol copolymer and the DMSO solvent. More particularly, tetrahydrofuran used as the wetting fluid can comprise from about 1% to about 44%, usefully about 21% by weight of the total weight of the solution. Dimethylformamide used as the wetting fluid can comprise from about 1% to about 80%, usefully about 8% by weight of the total weight of the solution. 1-butanol used as the wetting fluid can comprise from about 1% to about 33%, usefully about 9% by weight of the total weight of the solution. N-butyl acetate used as the wetting fluid can comprise from about 1% to about 34%, usefully about 14% by weight of the total weight of the solution. Dimethyl acetamide used as the wetting fluid can comprise from about 1% to about 40%, usefully about 20% by weight of the total weight of the solution.

Active Ingedient

In accordance with another embodiment, sufficient amounts of an active ingredient are dispersed in the blended composition of the ethylene vinyl alcohol copolymer and the DMSO solvent, without the wetting fluid. In this embodiment, the ethylene vinyl alcohol copolymer can comprise from about 0.1% to about 35%, usefully from about 12% to about 20% by weight of the total weight of the composition, the DMSO solvent can comprise from about 59.9% to about 99.8%, usefully from about 79% to about 87% by weight of the total weight of the composition, and the active ingredient can comprise from about 0.1% to about 40%, usefully from about 1% to about 9% by weight of the total weight of the composition. More than 9% by weight of the active ingredient can adversely affect characteristics that are desirable in the polymeric coating, such as adhesion of the coating to the prosthesis. Selection of a specific weight ratio of the ethylene vinyl alcohol copolymer and the DMSO solvent is dependent on factors such as the material from which the prosthesis is made, the geometrical structure of the prosthesis, and the type and amount of the active ingredient employed.

In accordance with another embodiment, sufficient amounts of the active ingredient are dispersed in the blended composition of the ethylene vinyl alcohol copolymer, the DMSO solvent, and the wetting fluid. In this embodiment, the ethylene vinyl alcohol copolymer can comprise from about 0.1% to about 35%, usefully from about 10% to about 25% by weight of the total weight of the composition, the DMSO solvent can comprise from about 19.8% to about 98.8%, usefully from about 49% to about 79% by weight of the total weight of the composition, the wetting fluid can comprise from about 1% to about 80%, usefully from about 5% to about 40% by weight of the total weight of the composition, and the active ingredient can comprise from about 0.1% to about 40%, usefully from about 1% to about 9% by weight of the total weight of the composition. Selection of a specific weight ratio of the ethylene vinyl alcohol copolymer, the DMSO solvent, and the wetting fluid is dependent on factors such as the material from which the prosthesis is made, the geometrical structure of the prosthesis, and the type and amount of the active ingredient employed.

The particular weight percentage of the active ingredient mixed within the composition, with or without the wetting fluid, depends on factors such as duration of the release, cumulative amount of release, and release rate that is desired. It is known that the release rate and the cumulative amount of the active ingredient that is released is directly proportional to the total initial content of the ingredient in the copolymer matrix. Accordingly, a wide spectrum of release rates can be achieved by modifying the ethylene comonomer content and the initial amount of the active ingredient. The active ingredient should be in true solution or saturated in the blended composition. If the active ingredient is not completely soluble in the composition, operations including mixing, stirring, and/or agitation can be employed to effect homogeneity of the residues. The active ingredient can also be first added to the wetting fluid prior to admixing with the composition. The active ingredient may be added so that dispersion is in fine particles. The mixing of the active ingredient can be conducted in an anhydrous atmosphere, at ambient pressure, and at room temperature such that supersaturating the active ingredient is not desired.

The active ingredient should inhibit the activity of vascular smooth muscle cells. More specifically, the active ingredient is aimed at inhibiting abnormal or inappropriate migration and proliferation of smooth muscle cells.

"Smooth muscle cells" include those cells derived from the medial and adventitia layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

"Migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

"Proliferation" of smooth muscle cells means increase in cell number.

"Abnormal" or "inappropriate" proliferation means division, growth or migration of cells occurring more rapidly or to a significantly greater extent than typically occurs in a normally functioning cell of the same type, i.e., hyperproliferation.

"Inhibiting" cellular activity means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. As used herein, the term "reducing" means decreasing the intimal thickening that results from stimulation of smooth muscle cell proliferation. "Delaying" means retarding the progression of the hyperproliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atheroectomy, or coronary artery bypass surgery. The effects of reducing, delaying, or eliminating restenosis may be determined by methods known to one of ordinary skill in the art, including, but not limited to, angiography, ultrasonic evaluation, fluoroscopy imaging, fiber optic visualization, or biopsy and histology. Biologically mediated vascular injury includes, but is not limited to injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanical mediated vascular injury includes, but is not limited to vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active ingredient of the invention is not restricted in use for therapy following vascular injury or trauma; rather, the usefulness of the active ingredient will also be determined by the ingredient's ability to inhibit cellular activity of smooth muscle cells or inhibit the development of restenosis.

In one embodiment, the active ingredient is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Actinomycin D is represented by the molecular formula $C_{62}H_{86}N_{12}O_{16}$, and is generally depicted by the following structure:

ACTINOMYCIN D

In an alternative embodiment, the active ingredient is a cocktail combination of actinomycin D, or analogs and derivatives thereof, and a therapeutic agent. The therapeutic agent includes any substance capable of exerting a therapeutic or prophylactic effect in the practice of the present invention. The therapeutic agents can also be for enhancing wound healing in a vascular site and improving the structural and elastic properties of the vascular site. Examples of such therapeutic agents include other antiproliferative substances as well as antineoplastic, antiinflammatory, antiplatelet, anticoagulant, antifibrin, antithrombin, antimitotic, antibiotic, antioxidant, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/

IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL, (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-COA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. Exposure of the ethylene vinyl alcohol/DMSO composition or ethylene vinyl alcohol/DMSO/wetting fluid composition to the therapeutic agent is not permitted to adversely alter the agent's composition or characteristic. Accordingly, the particular therapeutic agent is selected for mutual compatibility with the blended composition.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard phannacological test procedures to determine dosages are understood by one of ordinary skill in the art.

Prosthesis

The prosthesis used in conjunction with the above-described composition may be any suitable prosthesis, examples of which include self-expandable stents, balloon-expandable stents, and grafts. The underlying structure of the prosthesis can be virtually any design. The prosthesis can be made of a metallic material or an alloy such as, but not limited to, stainless steel, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Prostheses made from bioabsorbable or biostable polymers could also be used with the blended composition. A polymeric prosthesis should be compatible with the composition. The ethylene vinyl alcohol copolymer, however, adheres very well to metallic materials, more specifically to stainless steel.

Methods For Coating the Prosthesis Using The Composition

To form a coating on a surface of the prosthesis, the surface of the prosthesis should be clean and free from contaminants that may be introduced during manufacturing. However, the surface of the prosthesis requires no particular surface treatment to retain the applied coating. The composition can be applied to both the inner and outer (the tissue contacting) surfaces of the prosthesis. Application of the composition can be by any conventional method, such as by spraying the composition onto the prosthesis or immersing the prosthesis in the composition. The addition of a wetting fluid leads to a consistent application of the composition which causes the coating to be uniformly deposited on the surface of the prosthesis.

After the composition is applied, the prosthesis can be heated by, for example, passing the prosthesis over a hot plate. The prosthesis should be exposed to the heat for a short duration of time, typically about 3 to 5 seconds. The temperature of the hot plate can be from about 55° C. to about 65° C., typically about 60° C. Exposure of the prosthesis to the hot plate prevents the prosthesis from cooling at a rapid rate. Rapid cooling of the prosthesis may adversely affect properties that are generally desirable in a coating, such as elasticity. The polymer can be further exposed to heat treatment or cured for a predetermined duration of time, for example for about 6 hours. The heat treatment can be conducted generally at the same temperature range as the hot plate, for example from about 55° C. to about 65° C., typically about 60° C. The heat treatment prevents formation of air bubbles in the polymeric coating.

The DMSO solvent or the combination of the DMSO solvent and wetting fluid is removed from the composition on the surfaces of the prosthesis by allowing the DMSO solvent or combination of the DMSO solvent and wetting fluid to evaporate. The evaporation can be induced by heating the prosthesis at a predetermined temperature for a predetermined period of time. For example, the prosthesis can be heated at a temperature of about 60° C. for about 12 hours to about 24 hours. The heating can be conducted in an anhydrous atmosphere and at ambient pressure. The heating can, alternatively, be conducted under a vacuum condition. It is understood that essentially all of the DMSO solvent and the wetting fluid will be removed from the composition but traces or residues can remain blended with the copolymer.

Coating

The coating can be made from an ethylene vinyl alcohol copolymer and the active ingredient. The ethylene vinyl alcohol copolymer is a biocompatible coating, i.e., a coating which, in the amounts employed, is non-toxic, non-inflammatory, chemically inert, and substantially non-immunogenetic.

The inclusion of the active ingredient in the copolymer allows not only retention of the active ingredient on the prosthesis (e.g., a stent) during delivery and, if applicable, expansion of the prosthesis, but also controlled administration of the active ingredient following implantation. By way of example, and not limitation, the impregnated ethylene vinyl alcohol copolymer can have a thickness of about 0.5 microns to about 1.5 microns. The particular thickness of the copolymer is based on the type of procedure for which prosthesis is employed and the amount of the active ingredient that is desired to be delivered. The amount of the active ingredient to be included on the prosthesis can be further increased by applying a plurality of coating layers onto the prosthesis. The application of each layer should be performed subsequent to the evaporation of the DMSO solvent or DMSO/wetting fluid and the drying of the copolymer of the previous layer.

In one embodiment, a layer or a second coating formed from a polymeric material, free from the active ingredient or any therapeutic agents, is deposited on the active ingredient impregnated copolymer coating. Yet in another embodiment, a layer or a second coating formed from a polymeric material carrying at least one therapeutic agent, such as the aforementioned therapeutic agents, is deposited on the active ingredient impregnated copolymer coating. Suitable polymeric material can include, but are not limited to, polycaprolactone (PCL), poly-D,L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates, fibrin, fibrinogen, cellulose, starch, collagen, Parylene, PARYLAST, polyurethane, polyethylene, polyethylene teraphthalate, ethylene vinyl acetate, silicone, polyethylene oxide, and mixtures thereof.

In another embodiment, a layer or a second coating formed from essentially an ethylene vinyl alcohol copolymer, free from the active ingredient or any therapeutic agents, can be deposited on the active ingredient impregnated copolymer coating. Yet in another embodiment, a layer or a second coating formed from the ethylene vinyl alcohol copolymer carrying at least one therapeutic agent, such as the aforementioned therapeutic agents, can be deposited on the active ingredient impregnated copolymer coating. The ethylene vinyl alcohol copolymer used as a second coating can comprise a mole percent of ethylene of from about 27% to about 44%. It is understood by one of ordinary skill in the art that ethylene vinyl alcohol copolymer may also be a terpolymer so as to include small amounts of additionally monomers, for example less than about five (5) mole percentage of styrenes, propylene, and other suitable monomers.

The substance free second coating produces a membrane that reduces the rate of release of the active ingredient from the impregnated ethylene vinyl alcohol copolymer. The substance carrying second coating provides a method of administering any suitable number and combinations of therapeutic agents in combination with the active ingredient of the present invention.

If an ethylene vinyl alcohol copolymer is used as a rate reducing membrane, as a general rule, an increase in the amount of ethylene comonomer content of the second coating decreases the rate that the active ingredient can permeate through the matrices of the second coating. By way of example, and not limitation, the second coating can have a thickness of about 0.25 microns to about 1.5 microns. Typically, the second coating can have a thickness of about 1 micron. It is understood by one of ordinary skill in the art that the thickness of the layer is based on factors such as the type of procedure for which the prosthesis is employed and the rate of release that is desired.

Method of Use

In accordance with the above described method, the active ingredient can be applied to a prosthesis, e.g., a stent, retained on the stent during delivery and expansion of the stent, and released at a desired control rate and for a predetermined duration of time at the site of implantation. The release rate of the active ingredient can be controlled by modifying release parameters such as the amount of ethylene comonomer content of the copolymer and the initial active ingredient content in the copolymer. The rate of release can also be adjusted by the addition of second polymeric layer, with or without the active ingredient. A stent having the above described medicated coating is useful for a variety of medical procedures, including, by way of example, treatment of obstructions caused by tumors in bile ducts, esophagus, trachea/bronchi and other biological passageways. A stent having the above described medicated coating is particularly useful for treating occluded regions of blood vessels caused abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters and data are not be construed to unduly limit the scope of the embodiments of the invention.

Example 1

Multi-Link™ stents (available from Guidant Corporation) were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH: DMSO ratio of 1:7. The mixture was placed in a warm water shaker bath at 60° C. for 24 hours. The solution was cooled and vortexed. The cleaned Multi-link™ stents were dipped in the EVOH solution and then passed over a hot plate, for about 3–5 seconds, with a temperature setting of about 60° C. The coated stents were heated for 6 hours in an air box and then placed in an oven at 60° C., under vacuum condition, and for 24 hours. The coated stents were expanded on a 4.0 mm angioplasty balloon. The coatings remained intact on the stents. The coatings were transparent giving the Multi-Link™ stents a glossy-like shine.

Example 2

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 4 grams of DMSO, making an EVOH: DMSO ratio of 1:4. Dexamethasone was added to the 1:4 EVOH: DMSO solution. Dexamethasone constituted 9% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box and then placed in a vacuum oven at 66° C. for 24 hours. The above-recited step was repeated twice. The average weight of the coating was 0.0003 gram, having an estimated dexamethasone content of 75 ug per stent. The coated stents were expanded on a 4.0 mm angioplasty balloon. The coatings remained intact on the stents. Verification of coverage and physical properties of the coatings were visualized using a scanning electron microscope. The coatings were transparent, giving the Multi-Link™ stents a glossy-like shine.

Example 3

Multi-Link Duet™ stents are cleaned by placement in an ultrasonic bath of isopropyl alcohol solution for 10 minutes. The stents are dried and plasma cleaned in a plasma chamber. The EVOH solution is made with 1 gram of EVOH and 4 grams of DMSO, making an EVOH: DMSO ratio of 1:4. Dexamethasone is added to the 1:4 EVOH: DMSO solution. Dexamethasone constitutes 9% by weight of the total weight of the solution. The solution is vortexed and placed in a tube. The cleaned Multi-Link™ stents are attached to mandrel wires and dipped into the solution. The coated stents are passed over a hot plate, for about 3–5 seconds, with a temperature setting of about 60° C. The coated stents are cured for 6 hours in an air box then placed in a vacuum oven at 60° C. for 24 hours. The single layered dexamethasone/ EVOH coated stents are dipped into the 1:4 ratio EVOH:DMSO solution, free from dexamethasone. The stents are passed over the hot plate, cured, and placed in the oven as previously described. The top coating will provide a barrier layer for controlling the release of dexamethasone from the drug coated layer. The coated stents can be expanded on a 4.0 mm angioplasty balloon. It is predicted that the coatings will remain intact on the stents. The coatings will be transparent, giving the Multi-Link™ stents a glossy-like shine.

Example 4

Figure 2:
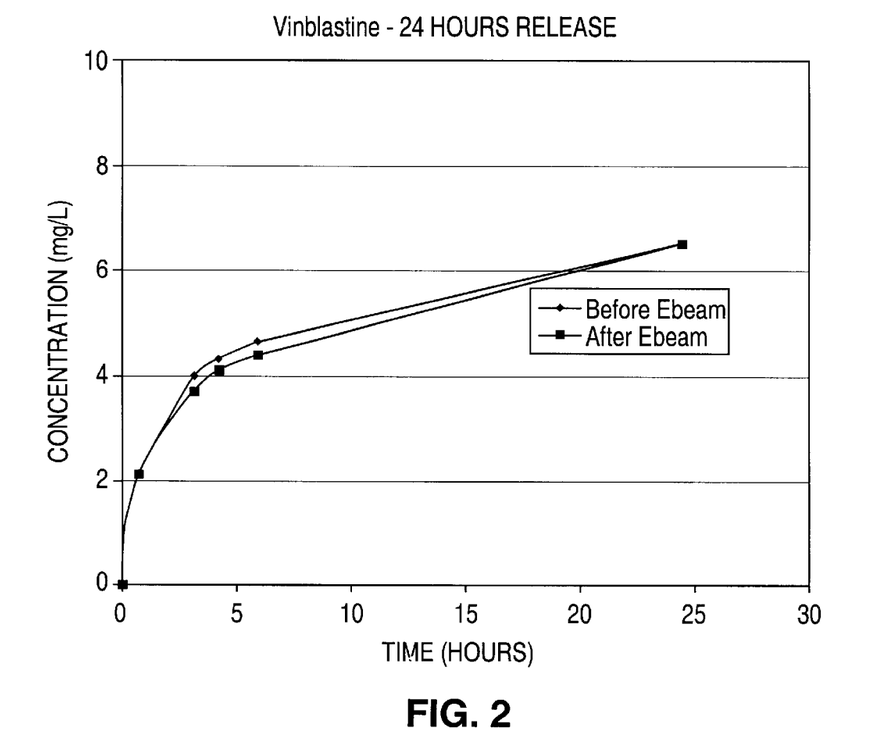
FIG. 2 graphically illustrates elution profiles for stents with a coating of ethylene vinyl alcohol copolymer impregnated with vinblastine made according to Example 4.

Multi-Link™ stents were cleaned by placement in an ultrasonic bath of isopropyl alcohol solution for 10 minutes. The stents were dried and plasma cleaned in a plasma chamber. An EVOH solution was made with 1 grain of EVOM and 7 grams of DMSO, making an EVOH: DMSO ratio of 1:7. Vinblastine was added to the 1:7 EVOH:DMSO solution. Vinblastine constituted 2.5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00005 gram, with an estimated vinblastine concentration of 12 microgram per stent. Some of the stents were sterilized by electron beam radiation. The sterilized and unsterilized vinblastine coated stents were tested for a 24 hour elution period by placing one sterilized and one unsterilized stent in 5 ml of phosphated saline solution (pH 7.4) at room temperature with rotational motion. The amount of vinblastine eluted was evaluated by High Performance Liquid Chromatography (HPLC) analysis. The results of this test are given below and plotted in FIG. 2. The data indicates that electron beam radiation procedure does not interfere in the release of vinblastine from EVOH.

| Release Profile For Vinblastine - Unsterilized | | | |
| --- | --- | --- | --- |
| Time (Hours) | microgram Released | Total microgram Released | microgram Release per Hour |
| 0 | 0 | 0 | 0 |
| 0.5 | 2.12 | 2.12 | 4.24 |
| 3 | 1.91 | 4.03 | 0.76 |
| 4 | 0.27 | 4.30 | 0.27 |
| 6 | 0.38 | 4.68 | 0.19 |
| 24 | 1.7 | 6.38 | 0.09 |
| Release Profile For Vinblastine - Sterilized | | | |
| Time (Hours) | ug Release | Total uG Released | uG Release per Hour |
| 0 | 0 | 0 | 0 |
| 0.5 | 2.14 | 2.14 | 4.28 |
| 3 | 1.7 | 3.84 | 0.68 |
| 4 | 0.28 | 4.12 | 0.28 |
| 6 | 0.26 | 4.38 | 0.13 |
| 24 | 2.05 | 6.43 | 0.11 |

Example 5

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH: DMSO ratio of 1:7. Cephalotaxin was added to the 1:7 EVOH: DMSO solution. Cephalotaxin constituted 5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00013 gram, with an estimated cephalotaxin concentration of 33 ug. The stents were sterilized by electron beam radiation. Cephalotaxin/ EVOH coated stents and EVOH-coated control stents were implanted in the coronary arteries of 4 pigs, generally in accordance to the procedure set forth in "Restenosis After Balloon Angioplasty-A Practical Proliferative Model in Porcine Coronary Arteries" by Robert S. Schwartz, et al., Circulation 82(6):2190–2200, December 1990, and "Restenosis and the Proportional Neointimal Response to Coronary Artery Injury: Results in a Porcine Model" by Robert S. Schwartz et al, J Am Coll Cardiol; 19:267–74 Feb. 1992. Results of the porcine artery study indicated that there was no significant difference between the uncoated, EVOH coated and cephalotaxin coated stents in the amount of neointimal proliferation resulting from arterial injury.

Example 6

Multi-Link Duet™ stents (available from Guidant Corporation) were cleaned by placement in an ultrasonic bath of isopropryl alcohol solution for 20 minutes, then air dried. An EVOH stock solution was made with 1 gram of EVOH and 7 grams of DMSO, making an EVOH: DMSO ratio of 1:7. The mixture was placed in a warm water shaker bath at 60° C. for 12 hours. The solution was mixed, then cooled to room temperature. A co-solvent was added to the EVOH solution to promote wetting of the struts of the Multi-Link Duet™ stents. One gram of tetrahydrofuran (THF) was mixed with 1.2 grams of the EVOH: DMSO solution. The cleaned Multi-Link Duet™ stents were attached to mandrel wires and dipped into the solution. The coated stents were passed over a hot plate, for about 3 to 5 seconds, with a temperature setting of about 60° C. The coated stents were then heated in a laboratory oven at 90° C. for 4 hours. The thin EVOH coating adhered to stainless steel without peeling or cracking. EVOH forms a superior primer base coat for other polymers that do not adhere well to stainless steel.

Example 7

Multi-Link Duet™ stents were cleaned in an ultrasonic bath of isopropyl alcohol for 20 minutes, then air dried. An EVOH solution was made with 1 gram of EVOH and 5 grams of DMSO, making an EVOH: DMSO ratio of 1:5. The mixture was placed in a warm water shaker bath at 60° C. for 12 hours. The solution was mixed, then cooled to room temperature. The dissolved EVOH: DMSO solution was mixed with 24.6 grams of THF and 19.56 grams of DMSO. The solution was mixed then placed in the reservoir of an air pressured atomizing sprayer. Multi-Link Duet™ stents were sprayed while the stents rotated between 30 to 120 rpm. The spray time was dependent upon the flow rate of the sprayer. A flow rate between 1 to 20 mg/second required a stent to be sprayed between 1 to 30 seconds. The polymer coated Multi-Link Duet™ stents were heated in a forced air convection oven for 12 hours. The coatings were transparent, giving the Multi-Link Duet™ stents a glossy-like shine.

Example 8

Multi-Link Duet™ stents were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. Various co-solvents were examined to determine which co-solvent would promote a thicker coating. These co-solvents were THF, DMF, 1-butanol, and n-butyl acetate. The formulation for the co-solvents was as follows. Three grams of dissolved EVOH: DMSO solution was mixed with 0.9 gram of THF; three grams of dissolved EVOH: DMSO solution was mixed with 0.39 gram of DMF; three grams of dissolved EVOH: DMSO solution was mixed with 0.5 gram of 1-butanol; and three grams of dissolved EVOH: DMSO solution was mixed with 0.68 gram of n-butyl acetate. The cleaned Multi-Link Duet™ stents, attached to mandrel wires, were dipped into the solutions. The coated stents were passed over a hot plate, for about 3 to 5 seconds, with a temperature setting of about 60° C. The coated stents were heated in a forced air convection oven for 24 hours. A second layer of coating was applied to coated Multi-Link Duet™ stents and the stents were heated in the same manner as above. No difference was seen between the stents coated with the various co-solvents (e.g., greater weight of coating or physical appearance). All coated stents were transparent, giving the Multi-Link Duet™ stents a glossy-like shine. No webbing or bridging of the coating was seen between the struts of the coated Multi-Link Duet™ stents. The weight of the coatings was between 0.2 to 0.27 mg/stent.

Example 9

Multi-Link Duet™ stents are cleaned in an ultrasonic bath of isopropyl alcohol for 20 minutes, then air dried. An EVOH stock solution is made having an EVOH: DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVOH: DMSO solution is mixed with 0.29 gram of Dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 10

Multi-Link Duet™ stents are cleaned in an ultrasonic bath of isopropyl alcohol for 20 minutes, then air dried. An EVOH stock solution is made having an EVOH: DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVOH: DMSO solution is mixed with 0.29 gram of Dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 11

Multi-Link Duet™ stents were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. A 4.75% by weight actinomycin D solution was formulated as follows: 600 milligrams of the EVOH: DMSO solution was mixed with 40 milligrams of actinomycin D, then 200 milligrams of THF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 12

Multi-Link Duet™ stents were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. A 3.60% by weight actinomycin D solution was formulated as follows: 600 milligrams of the EVOH: DMSO solution was mixed with 40 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 13

Multi-Link Duet™ stents were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. A 6.45% by weight actinomycin D solution was formulated as follows: 680 milligrams of the EVOH: DMSO solution was mixed with 80 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 14

Multi-Link Duet™ stents are cleaned in an ultrasonic bath of isopropyl alcohol for 20 minutes, then air dried. An EVOH stock solution is made having an EVOH: DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH: DMSO solution is mixed with 40 milligrams of Actinomycin D, then 2000 milligrams of THF is added. The cleaned Multi-Link Duet™ stents can be sprayed upon by the above formulation. The coated stents are cured in a forced air convection oven for 2 hours. A second layer of coating is applied and cured in the above manner.

Example 15

Inhibition of SMC Proliferation With Actinomycin D

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3–4. SMC monlayers were established on 24 well culture dishes, scrape wounded and treated with actinomnycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 3.

Figure 3:
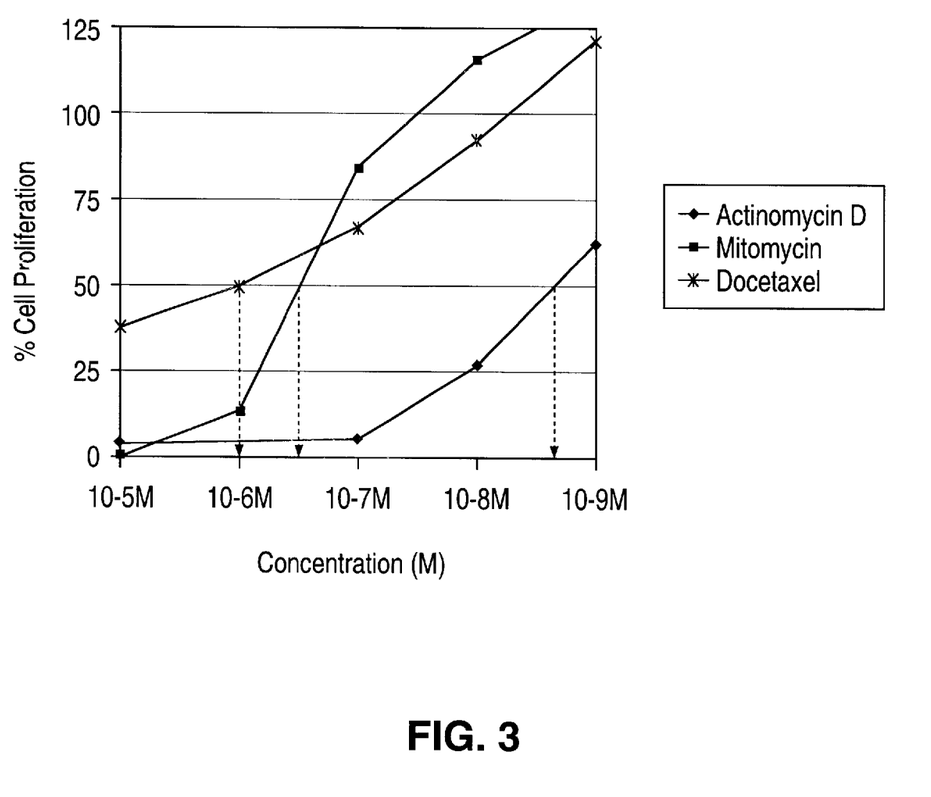
FIG. 3 graphically illustrates in vitro experimental data, in accordance with Example 16, showing affects of actinomycin D, mitomycin, and docetaxel on smooth muscle cell proliferation.

The $IC_{50}$ (concentration at which 50% of the cells stop proliferating) of actimomycin D was $10^{-9}M$ as compared to $5 \times 10^{-5}M$ for mitomycin and $10^{-6}M$ for docetaxel. Actinomycin D was the most potent agent to prevent SMC proliferation as compared to other pharmaceutical agents.

Example 16

Reduction in Restenosis in the Porcine Coronary Artery Model

Porcine coronary models were used to assess the degree of the inhibition of neointimal formation in the coronary arteries of a porcine stent injury model by Actinomycin D, delivered with a microporous balloon catheter ($1 \times 10^6$ pores/$mm^2$ with sizes ranging from 0.2–0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. The drug was delivered to the denuded sites at 3.5 atm (3.61 Kg/sq cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry.

Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100(IEL\ area - lumen\ area)/IEL\ area$$

where IEL is the internal elastic lamia.

Figure 4A:
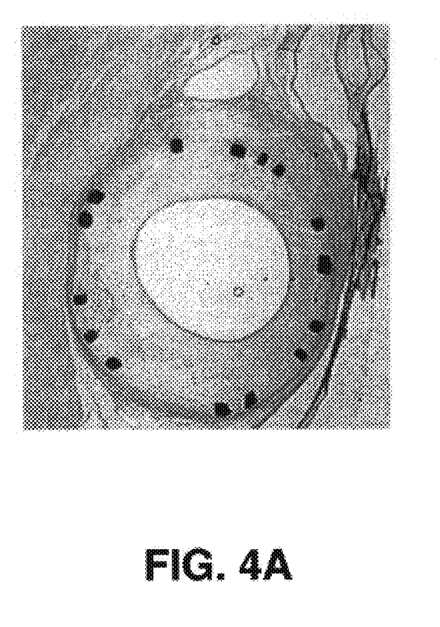
FIG. 4A is a picture of a histology slide of a coronary vessel from the control group in accordance with Example 17.
Figure 4B:
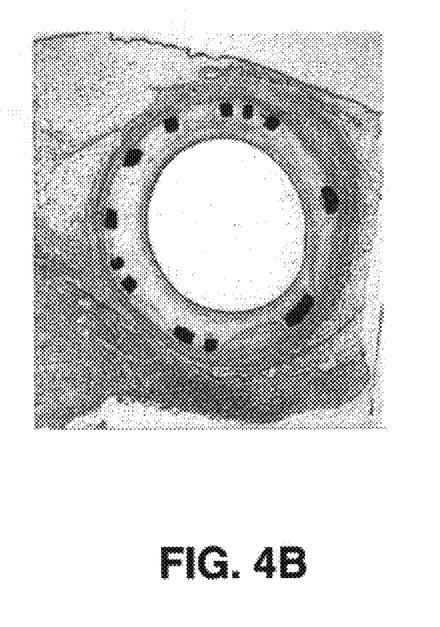
FIG. 4B is a picture of a histology slide of a coronary vessel from the actinomycin D group in accordance with Example 17.

The control group of animals received delivery of water instead of the drug. The test group of animals received actinomycin D in two different concentration of $10^{-5}M$ and $10^{-4}M$. The results of the study are tabulated in Table 1. The percent stenosis in the treated groups (32.3+/−11.7) was significantly decreased as compared to the control groups (48.8+/−9.8). FIGS. 4A and 4B illustrate sample pictures of the histology slides of the coronary vessels from the control and the Dose 1 group, respectively.

60° C. for 1 hour. A second layer of coating was applied in the above manner and cured in a forced air convection oven at 60° C. for 4 hours. An average coating weight of about 260 micrograms and an average actinomycin D loading of about 64 micrograms was achieved.

Example 18

Multi-Link Duet™ stents (13 mm in length) were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. A 3.75% by weight actinomycin D solution was formulated as follows: 60 milligrams of actinomycin D was dissolved in 310 milligrams of DMF, then 1.22 grams of EVOH: DMSO solution was added. The cleaned Multi-Link Duet™ stents were attached to mandrel wires and dipped into the solution.

TABLE 1

|  | CONTROL 0M | DOSE 1 1E-05M | DOSE 2 1E-04M | t test (significant if $p < 0.05$) | |
|---|---|---|---|---|---|
|  | (n = 9) | (n = 10) | (n = 7) | p~ | p* |
| ANGIOGRAPHIC DATA (QCA) | | | | | |
| Percent Diameter Stenosis | 48.8 +/− 9.8 | 36.8 +/− 9.7 | 32.3 +/− 11.7 | 0.02 | 0.01 |

|  | CONTROL 0M | DOSE 1 1E-05M | DOSE 2 1E-04M | t test (significant if $p < 0.05$) | |
|---|---|---|---|---|---|
|  | (n = 27) | (n = 30) | (n = 21) | p~ | p* |
| HISTOMORPHOMETRIC DATA | | | | | |
| Percent Stenosis (IEL area-lumen area)/ IEL area | 63.4 +/− 12.7 | 51.8 +/− 13.8 | 54.1 +/− 11.7 | 0.002 | 0.01 |
| Residual Lumen (Lumen area)/ IEL area | 0.36 +/− 0.16 | 0.49 +/− 0.14 | 0.46 +/− 0.08 | 0.002 | 0.01 |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

Example 17

Multi-Link Duet™ stents (13 mm in length) were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. A 5.06% by weight actinomycin D solution was formulated as follows: 40 milligrams of actinomycin D was dissolved in 150 milligrams of THF, then 600 milligrams of the EVOH: DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 270 micrograms with an average actinomycin D content of about 51 micrograms was achieved.

Example 19

Multi-Link,Duet™ stents were cleaned in an ultrasonic bath of isopropyl alcohol for 20 minutes, then air dried. An EVOH stock solution was made having an EVOH: DMSO ratio of 1:4. The mixture was placed in a warm water shaker bath at 60° C. for 12 hours. The solution was mixed, then cooled to room temperature. A 6.1% by weight actinomycin D solution was formulated as follows: 100 milligrams of actinomycin D was dissolved in 310 milligrams of DMF, then 1.22 grams of EVOH: DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 250 micrograms and an average actinomycin D loading of about 75 micrograms was achieved.

Example 20

Multi-Link Duet™ stents are cleaned in an ultrasonic bath of isopropyl alcohol for 20 minutes, then air dried. An EVOH stock solution is made having an EVOH: DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH: DMSO solution is mixed with 40 milligrams of Actinomycin D, then 2000 milligrams of THF is added. The cleaned Multi-Link Duet™ stents can be sprayed upon by the above formulation. The coated stents are cured in a forced air convection oven 60° C. for 15 minutes. Additional layers of the coating are applied and cured in the above manner. The final curing step for the coated stents is conducted for about 4 hours.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A coating for a stent, comprising a layer of an ethylene vinyl alcohol copolymer containing actinomycin D or analogs or derivatives thereof and a layer of an ethylene vinyl alcohol copolymer free from actinomycin D disposed beneath the layer of the ethylene vinyl alcohol copolymer containing the actinomycin D, wherein the layer of the ethylene vinyl alcohol copolymer free from the actinomycin D is disposed on a surface of the stent.

2. The coating of claim 1, wherein the stent is selected from a group of balloon-expandable stents, self-expandable stents, and grafts.

3. The coating of claim 1, wherein the layer of the ethylene vinyl alcohol copolymer containing the actinomycin D is made from a composition comprising:
   (a) an ethylene vinyl alcohol copolymer constituting from about 0.1% to about 35% by weight of the total weight of the composition;
   (b) a dimethylsulfoxide solvent constituting from about 59.9% to about 99.8% by weight of the total weight of the composition; and
   (c) actinomycin D, or analogs or derivatives thereof, constituting from about 0.1% to about 40% by weight of the total weight of the composition;
   wherein after the composition is applied to the stent, the dimethylsulfoxide solvent is essentially removed from the composition on the stent to form the layer.

4. The coating of claim 1, wherein the layer of the ethylene vinyl alcohol copolymer containing the actinomycin D is made from a composition comprising:
   (a) an ethylene vinyl alcohol copolymer constituting from about 0.1% to about 35% by weight of the total weight of the composition;
   (b) a dimethylsulfoxide solvent constituting from about 19.8% to about 98.8% by weight of the total weight of the composition;
   (c) a fluid having a contact angle of less than about 90°, the fluid constituting from about 1% to about 80% by weight of the total weight of the composition; and
   (d) actinomycin D, or analogs or derivatives thereof, constituting from about 0.1% to about 40% by weight of the total weight of the composition;
   wherein after the composition is applied to the stent, the dimethylsulfoxide solvent and the fluid are essentially removed from the composition on the stent to form the layer.

5. The coating of claim 4, wherein the fluid is selected from a group of tetrahydrofuran, dimethylformamide, 1-butanol, n-butyl acetate, dimethyl acetamide, and mixtures thereof.

6. The coating of claim 1, additionally comprising a therapeutic substance carried by the layer of the ethylene vinyl alcohol copolymer containing the actinomycin D to be released in combination with the actinomycin D or analogs or derivatives thereof.

7. The coating of claim 6, wherein the therapeutic substance is selected from a group of antineoplastic, antiinflammatory, antiplatelet, anticoagulant, antifibrin, antithrombin, antimitotic, antiproliferative, antibiotic, antioxidant substances, and combinations thereof.

8. The coating of claim 6, wherein the layer of the ethylene vinyl alcohol copolymer containing the actinomycin D and the therapeutic substance is made from a composition comprising:
   (a) an ethylene vinyl alcohol copolymer constituting from about 0.1% to about 35% by weight of the total weight of the composition;
   (b) a dimethylsulfoxide solvent constituting from about 59.9% to about 99.8% by weight of the total weight of the composition; and
   (c) actinomycin D, or analogs or derivatives thereof, in combination with the therapeutic substance, constituting from about 0.1% to about 40% by weight of the total weight of the composition;
   wherein after the composition is applied to the stent, the dimethylsulfoxide solvent is essentially removed from the composition on the stent to form the layer.

9. The coating of claim 6, wherein the layer of the ethylene vinyl alcohol copolymer containing the actinomycin D and the therapeutic substance is made from a composition comprising:
   (a) an ethylene vinyl alcohol copolymer constituting from about 0.1% to about 35% by weight of the total weight of the composition;
   (b) a dimethylsulfoxide solvent constituting from about 19.8% to about 98.8% by weight of the total weight of the composition;
   (c) a fluid having a contact angle of less than about 90°, the fluid constituting from about 1% to about 80% by weight of the total weight of the composition; and
   (d) actinomycin D or analogs or derivatives thereof, in combination with the therapeutic substance, constituting from about 0.1% to about 40% by weight of the total weight of the composition;
   wherein after the composition is applied to the stent, the dimethylsulfoxide solvent and the fluid are essentially removed from the composition on the stent to form the layer.

10. The coating of claim 9, wherein the fluid is selected from a group of tetrahydrofuran, dimethylformamide, 1-butanol, n-butyl acetate, dimethyl acetamide, and mixtures thereof.

11. A method of forming a coating for a stent, comprising the acts of:
applying a composition including an ethylene vinyl alcohol copolymer, the composition being free from any therapeutic substances, on a surface of the stent to form a layer of the ethylene vinyl alcohol copolymer free from any therapeutic substances on the surface of the stent; and
applying a composition comprising an ethylene vinyl alcohol copolymer and actinomycin D or analogs or derivatives thereof to the stent to form a layer of the ethylene vinyl alcohol copolymer containing the actinomycin D on the layer of the ethylene vinyl alcohol copolymer free from therapeutic substances.

12. The method of claim 11, wherein the stent is selected from a group of balloon-expandable stents, self-expandable stents, and grafts.

13. A coating for a prosthesis produced in accordance with the method of claim 11.

14. The method of claim 11, wherein the composition containing the actinomycin D additionally comprises a solvent such that the evaporation of the solvent causes the ethylene vinyl alcohol copolymer to solidify.

15. A coating for a prosthesis produced in accordance with the method of claim 14.

16. The method of claim 14, wherein the solvent comprises dimethylsulfoxide.

17. The method of claim 16, wherein for the composition comprising the actinomycin D, the ethylene vinyl alcohol copolymer constitutes from about 0.1% to about 35% by weight of the total weight of the composition, the dimethylsulfoxide constitutes from about 59.9% to about 99.8% by weight of the total weight of the composition, and the actinomycin D, or analogs or derivatives thereof, constitutes from about 0.1% to about 40% by weight of the total weight of the composition.

18. The method of claim 14, wherein the solvent comprises dimethylsulfoxide and a wetting fluid, the wetting fluid is selected from a group of tetrahydrofuran, dimethylformamide, 1-butanol, n-butyl acetate, dimethyl acetamide, and mixtures thereof.

19. The method of claim 18, wherein for the composition comprising the actinomycin D, the ethylene vinyl alcohol copolymer constitutes from about 0.1% to about 35% by weight of the total weight of the composition, the dimethylsulfoxide solution constitutes from about 19.8% to about 98.8% by weight of the total weight of the composition, the wetting fluid constitutes from about 1% to about 80% by weight of the total weight of the composition, and the actinomycin D or analogs or derivatives thereof constitutes from about 0.1% to about 40% by weight of the total weight of the composition.

20. The method of claim 14, wherein the solvent comprises dimethylsulfoxide and a wetting fluid, the wetting fluid having a contact angle less than about 90°.

21. The method of claim 20, wherein for the composition comprising the actinomycin D, the ethylene vinyl alcohol copolymer constitutes from about 0.1% to about 35% by weight of the total weight of the composition, the dimethylsulfoxide solution constitutes from about 19.8% to about 98.8% by weight of the total weight of the composition, the wetting fluid constitutes from about 1% to about 80% by weight of the total weight of the composition, and the actinomycin D or analogs or derivatives thereof constitutes from about 0.1% to about 40% by weight of the total weight of the composition.

22. The method of claim 11, wherein the composition comprising the actinomycin D additionally comprises a therapeutic substance used in combination with the actinomycin D or analogs or derivatives thereof, the therapeutic substance is selected from a group of antineoplastic, antiinflammatory, antiplatelet, anticoagulant, antifibrin, antithrombin, antimitotic, antiproliferative, antibiotic, antioxidant substances, and combinations thereof.

23. A coating for a prosthesis produced in accordance with the method of claim 22.

24. A stent comprising a radially expandable body and an ethylene vinyl alcohol coating, the coating comprises a region containing an active agent and a region free from any active agents disposed beneath the region containing the active agent, wherein the region that is free from any active agents is in contact with an outer surface of the stent.

25. The stent of claim 24, wherein the body is made from a metallic material.

26. The stent of claim 24, wherein the body is made from stainless steel.

27. The stent of claim 24, wherein the body is balloon-expandable or self-expandable.

28. The stent of claim 24, wherein the active agent is actinomycin D.

29. The method of claim 11, wherein the composition of the ethylene vinyl alcohol free from the therapeutic substances consists of from about 0.1% to about 35% by weight of an ethylene vinyl alcohol copolymer and from about 65% to about 99.0% by weight of a solvent or combination of solvents.

30. The method of claim 11, wherein the composition of the ethylene vinyl alcohol free from the therapeutic substances consists of from about 0.1% to about 35% by weight of an ethylene vinyl alcohol copolymer, from about 19.9% to about 98.9% by weight of a solvent, and from about 1% to about 80% by weight of a fluid having a contact angle less than about 90°.

* * * * *

UNITED STATES PATENT AND TRADEMARK OFFICE
CERTIFICATE OF CORRECTION

PATENT NO.    : 6,503,954 B1
DATED         : January 7, 2003
INVENTOR(S)   : Bhat et al.

It is certified that error appears in the above-identified patent and that said Letters Patent is hereby corrected as shown below:

Column 23,
Lines 18 and 24, change "prosthesis" to -- stent --.

Column 24,
Line 22, change "prosthesis" to -- stent --.

Signed and Sealed this

Seventeenth Day of June, 2003

JAMES E. ROGAN
*Director of the United States Patent and Trademark Office*